United States Patent [19]
Doiron et al.

[11] Patent Number: 5,728,092
[45] Date of Patent: Mar. 17, 1998

[54] LIGHT DELIVERY CATHETER

[75] Inventors: Daniel R. Doiron, Santa Ynez; David E. Mai, Santa Barbara, both of Calif.

[73] Assignee: Miravant Systems, Inc., Santa Barbara, Calif.

[21] Appl. No.: 611,590

[22] Filed: Mar. 7, 1996

[51] Int. Cl.⁶ ............................................ A61B 17/36
[52] U.S. Cl. ................................... 606/15; 606/11
[58] Field of Search ............................ 606/9, 10, 12, 606/14, 15, 16, 17

[56] References Cited

U.S. PATENT DOCUMENTS

| | | | |
|---|---|---|---|
| 5,098,427 | 3/1992 | Hessel et al. | 606/11 |
| 5,125,925 | 6/1992 | Lundahl | 606/15 |
| 5,151,096 | 9/1992 | Khoury | 606/15 |
| 5,196,005 | 3/1993 | Doiron et al. | 606/7 |
| 5,217,454 | 6/1993 | Khoury | 606/7 |
| 5,226,430 | 7/1993 | Spears et al. | 606/15 |
| 5,267,995 | 12/1993 | Doiron et al. | 606/15 |
| 5,269,777 | 12/1993 | Doiron et al. | 606/7 |
| 5,269,779 | 12/1993 | Sogawa et al. | 606/15 |
| 5,298,026 | 3/1994 | Chang | 606/15 |
| 5,334,207 | 8/1994 | Gay, Jr. | 606/7 |
| 5,449,354 | 9/1995 | Konwitz et al. | 606/15 |
| 5,454,782 | 10/1995 | Perkins | 606/15 |
| 5,536,265 | 7/1996 | vanden Bergh et al. | 606/2 |

*Primary Examiner*—Jennifer Bahr
*Assistant Examiner*—Sonya Harris-Ogugua
*Attorney, Agent, or Firm*—Michael G. Petit

[57] ABSTRACT

A light delivery catheter having an elongate, flexible inner tube coaxially disposed within a lumen within a flexible outer tube, and axially movable with respect to the outer tube. An optical waveguide disposed within the inner tube conducts light from an external light source to a light diffuser element in optical communication with the distal end of the optical waveguide. A portion of the light conducted to the diffuser element is scattered radially into the surrounding volume. The outer diameter of the inner tube is less than the diameter of the outer tube lumen, the annular space therebetween forming a cylindrical lumen coextensive with the inner tube. One or more fiber optics disposed within the cylindrical lumen are attached to the outer surface of the inner tube and terminate distally in an isotropic tip. Fiber optic bending means, responsive to advancement of the inner tube within the outer tube, causes the distal tips of the fiber optics to bend radially outward, as the distal tip of the inner tube emerges from the confines of the outer tube lumen. In operation, the distal tip of the outer tube is positioned within a body cavity. The inner tube is advanced through the outer tube lumen until the element and the distal tips of the fiber optics project beyond distal end of the outer tube. Therapeutic light from an external source is conducted from the proximal end of the optical waveguide to the diffuser element. The diffuser element scatters a portion the light radially, a portion of the radially scattered light being picked up by the fiber optic tips which are in contact with the tissue on the inner surface of the body cavity. The portion of light entering the isotropic tips is conducted to the proximal end of the catheter via the respective fiber optics for light detection and measurement.

2 Claims, 1 Drawing Sheet

5,728,092

LIGHT DELIVERY CATHETER

BACKGROUND OF THE INVENTION

1. Field of the Invention

This invention relates to invasive catheters delivering light to tissue within the body of an animal and more particularly to a light delivery catheter including means for monitoring therapeutic light incident upon the tissue.

2. Prior Art

Invasive light delivery catheters are well known in the art. Such catheters are used for conducting light from an external light source to remote portions of the body. Such light delivery catheters generally have a proximal end, a distal end and an elongate body portion therebetween housing a light conducting means. Such catheters are dimensioned so that they may be introduced and advanced through a tubular tissue within the body such as a blood vessel or the urethra to deliver therapeutic light to a diseased target tissue within the body.

Phototherapy of diseased tissue may proceed by various mechanisms such as ablation, photodynamic therapy, or hyperthermia. Photodynamic therapy is a procedure wherein a photosensitive molecule is administered to a patient thereafter to be present within a target tissue. The photosensitive molecules within the target tissue are then illuminated with phototherapeutic light having a wavelength operable for interacting with the photosensitive molecule in such a manner as to produce a photoactivated species possessing therapeutic properties. The photoactivated species thus formed either destroys cells or arrests physiologic activity in the associated diseased tissue thereby effecting a treatment of the target tissue.

A problem associated with administering phototherapy in general, and photodynamic therapy in particular to a diseased tissue is accurate dosimetry; that is, establishing when an effective dose of light has been administered to cure the diseased target tissue. For example, the amount of photodynamic therapy administered to a target tissue depends on the number of photoactivated species produced which, in turn, depends upon the amount or concentration of photosensitizer accumulated within the tissue as well as the amount of light delivered to the photosensitizer. Thus, the photosensitive reaction, which is responsible for the therapeutic tissue effects sought is a second order reaction. The rate of formation of photoactivated therapeutic species within a target tissue undergoing phototherapy is proportional to both the intensity of the light reaching the tissue and the concentration of photosensitive or photoreactive precursors within the diseased target tissue.

The amount of therapeutic light delivered to the target tissue is, in general, inversely proportional to the square of the distance of the light source from the target tissue. That is; excluding light loss due to absorption or scattering of therapeutic light by non-target intervening media, the intensity of treatment reaching a target tissue is inversely proportional to the square of the distance between the light source and the target tissue. Due to relative uncertainty in the distance between a source of light such as a light diffuser element and the target tissue undergoing treatment, the quadratic reduction in the intensity of light reaching a target tissue with respect to the distance between the source of light and target tissue makes it difficult to establish the precise amount of light administered to a target tissue during phototherapy.

To overcome such difficulties, Lundahl, in U.S. Pat. No. 5,125,925, the content of which patent is incorporated herein by reference thereto, describes an invasive balloon catheter operable for delivering uniform light to a target tissue. The catheter includes an optical waveguide terminating distally in a light diffuser element which diffuser element is surrounded by an inflatable transparent balloon. In operation, when the distal tip of the Lundahl catheter is advanced to position the diffuser element and overlying balloon within spherical body cavity, the balloon is inflated. In order to deliver uniform illumination to the tissue surrounding the balloon wall, the balloon is spherical when inflated, with the light source disposed at the center of the sphere to assure all portions of the surface undergoing treatment are equidistant from the source. Incorporated within or affixed to the wall of the balloon are the distal termini of optical fibers (pick-up fibers) which are operable for receiving a portion of the light reaching the wall of the balloon and for conducting the received portion of light to the proximal end of the catheter thereafter to be measured. Thus, because the balloon is inflated until the transparent wall of the balloon presses against the target tissue being illuminated, the portion of light reaching the spherical wall of the target tissue may be monitored by means of the isotropic fiber optic probe termini embedded in, or otherwise affixed to, the wall of the balloon. The catheter's operation requires a non-distendible balloon having one or more optical fibers with the distal tips thereof either imbedded within the balloon wall or attached to the wall of the balloon. The shape limitation imposed on the treated tissue by the inflated balloon limits the applicability of the catheter for delivering therapeutic light to substantially spherical hollow tissue. The catheter cannot be used to measure light delivered to hollow tissue having an irregularly shaped interior without distorting the tissue and compressing a portion thereof impairing blood circulation within the tissue which can effect phototherapy. In addition, affixing the tip of the pick-up fiber(s) to the wall of the balloon severely limits the amount of balloon expansion possible during inflation, if the wall of the balloon is distendible such as formed from elastic rubber, the fiber will break upon inflation. The balloon is limited to a collapsible/inflatable sphere pre-formed from a substantially non-distendible elastomer.

There are occasions when inflating a balloon around a light diffuser element in order to effect phototherapy is not practical as for performing phototherapy of brain tissue where tissue compression can cause ischemia and irreversible damage to normal tissue or inhibit PDT due to impaired blood circulation in the tissue. It is therefore desirable to provide a light delivery catheter which permits the operator to sample the light incident upon a diseased target tissue undergoing phototherapy either employing the inflation of a distendible balloon or without requiring any balloon whatsoever.

SUMMARY OF THE INVENTION

It is an object of the invention to provide a light delivery catheter for delivering therapeutic light to a tissue within the body.

It is yet a further object of this invention to provide a flexible elongate light delivery catheter having a proximal end and a distal end adapted for insertion within the body of an animal with means disposed near the distal end for the diffuse delivery of light to a diseased target tissue.

It is yet a further object of the invention to provide a light delivery catheter operable for delivering therapeutic light from an external light source to a diseased target tissue within a body, the catheter including means operable for sampling a portion of the therapeutic light which is incident upon a diseased target tissue.

The features of the invention believed to be novel are set forth with particularity in the appended claims. However, the invention itself both as to organization and method of operation, together with further objects and advantages thereof may best be understood by reference to the following description taken in conjunction with the accompanying drawings in which:

DESCRIPTION OF THE PREFERRED EMBODIMENT

Figure 1:
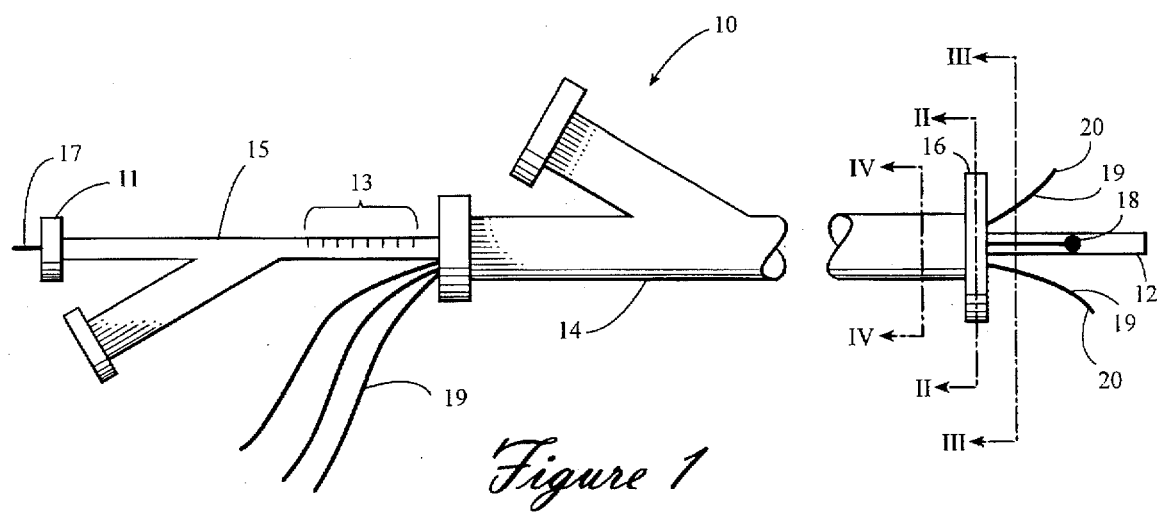
FIG. 1 is a partially cross-sectional horizontal view of a particular embodiment of light delivery catheter in accordance with the present invention.
Figure 2:
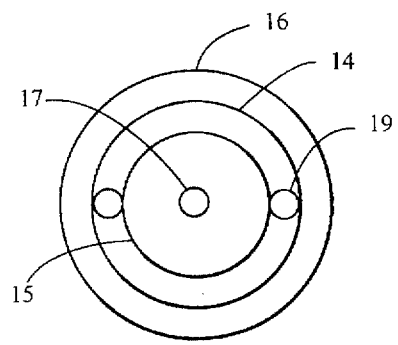
FIG. 2 is a vertical cross-sectional view of the catheter in accordance with the present invention along section line II—II of FIG. 1.
Figure 3:
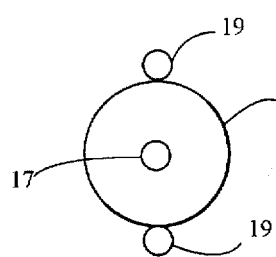
FIG. 3 is a vertical cross-sectional view of the inner tube portion along section line III—III of FIG. 1.
Figure 4:
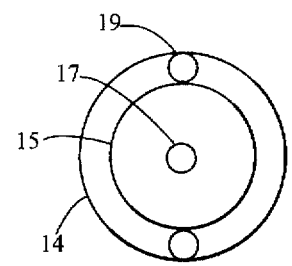
FIG. 4 is a vertical cross-sectional view of the outer tube portion along section line IV—IV of FIG. 1.

Turning first to FIG. 1, a catheter 10 in accordance with the present invention comprises an elongate member having a proximal end 11 and a distal end 12 and a body portion therebetween. The body portion comprises a hollow flexible outer tube 14 and a coaxially mounted inner tube 15 slideably disposed within the outer tube 14. The hollow outer tube 14 may further include an inflatable element 16 affixed to the distal end thereof and means (not shown) for inflating the element 16.

The inner tube 15 which is slideably disposed within the axial lumen of the outer tube 14, is an elongate flexible member comprising a treatment light-conducting optical waveguide 17, such as a fiber optic or fiber optic bundle having a proximal end adapted to receive light from a light source (not shown) and a distal end. A light diffuser element 18 is disposed to be in optical communication with the distal end of the optical waveguide 17. The optical waveguide 17 conducts light from an external light source (not shown) to the light diffuser element 18 on or near the distal tip thereof. The light incident upon the diffuser element 18 is redirected by scattering or reflection to exit the catheter in a desired pattern as the light traverses the diffuser element 18.

The inner tube 15 further comprises a plurality of light-collecting pick-up fibers 19 or sensors, the light-collecting pick-up fibers 19 comprising one or more fiber optics having distal light-sensing tips 20 which tips 20 are operable as isotropic light-receiving probes. The tips 20 can be used to monitor light incident thereon and derived from the diffuser element or fluorescence light emitted by photoactivated molecules in tissue. A portion of the length of the light-collecting optical fibers near the proximal end of the light-collecting optical fibers is affixed to the outer surface of the inner tube 15. The distal tip 20 of the light-collecting pick-up fibers 19 are adapted to receive light incident thereupon from an external source and conduct the light to the proximal end thereof. At least the most distal portion of the light-collecting pick-up fibers 19 are not affixed to the outer surface of the inner tube. The non-affixed distal portion of the length of the light-collecting optical fibers is free to flex or curl radially outward, away from central long axis of the inner tube 15 and diffuser element 18. When the inner tube 15 is advanced through the central lumen of the outer tube 14, the optical waveguide's 17 light diffuser element 18 and the distal tips 20 of the light-collecting pick-up fibers 19 emerge from the open distal end of the outer tube 14. The distal ends 20 of the light-collecting optical fibers 19, being no longer confined radially by the inner surface of the outer tube 14, curl radially outward, extending away from the light diffuser element 18 as the inner tube 15 is advanced.

Figure 5:
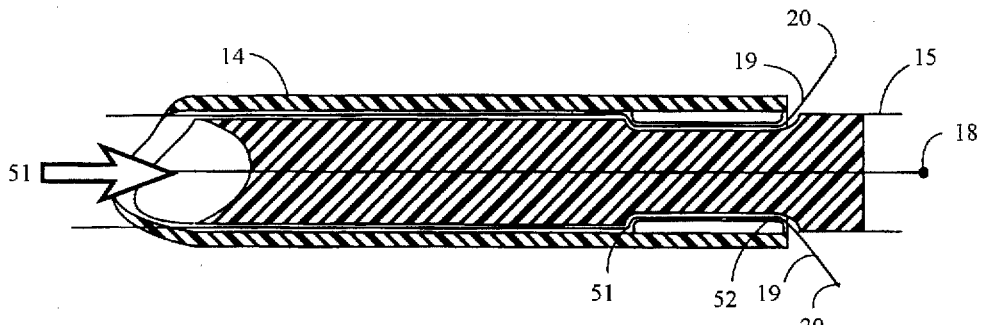
FIG. 5 is a fragmentary elevational cross-sectional view of an embodiment of the present catheter showing mechanical means for flexing the distal end of the pick-up fibers as the emerge from the distal end of the outer tube.
Figure 6:
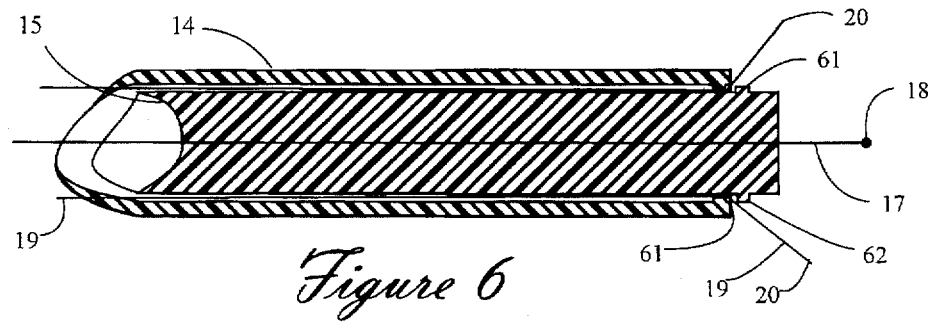
FIG. 6 is a fragmentary elevational cross-sectional view of another embodiment of the present catheter showing mechanical means for flexing the distal end of the pick-up fibers as the distal end of the pick-up fibers emerge from and project beyond the distal end of the outer tube.

Although the optical fibers employed as pick-up probes may be prestressed to present as a curved or bent fiber optic in a relaxed environment, it may be preferable to use straight flexible fiber optics for pick-up fibers and employ mechanical means to flex the fiber tips. Examples of mechanical means which may be employed to cause the distal tips of the fiber optics to flex radially outward as the inner tube is advanced distally through the outer tube are shown in FIGS. 5 and 6. Turning first to FIG. 5, as the inner tube 15 is advanced in the direction of the broad arrow 51, the light diffuser element 18 affixed to the distal end of the inner tube 15 emerges from the distal end of the outer tube 14 in the forward direction. As the distal ends 20 of the light-collecting pick-up fibers 19 emerge from the distal end of the outer tube 14 the pick-up fibers 19 are forced to flex radially outward in the direction of the broad arrows 52 by an inclined notch 53 cut within the outer surface of the inner tube 15 in which a portion of the pick-up fibers 19 lie.

FIG. 6 employs an annular ridge 61 on the interior surface of the distal end of the outer tube 14 as a fulcrum to bend the light-collecting pick-up fibers 19 as the inner tube 15 is advanced until an annular convex ridge 62 on the outer surface of the distal end of the inner tube 15 passes therethrough. The pick-up fibers may also be attached to spring wires (not shown) to force the fibers to flex radially.

In practice, the distal tip 12 of the catheter 10 is inserted into a lumen of the body such as the urethra and advanced therethrough until the distal end 12 enters a cavity such as the bladder. An optional inflatable member 16 positioned proximal to the distal tip 12 is inflated to releasably secure the distal tip of the catheter 10 within the cavity. The catheter has a multiplicity of light-collecting optical fibers 19 disposed therewithin. Each of the light-collecting pick-up fibers 19 have an isotropic light gathering tip 20 which tip 20 is operable for receiving a portion of the light from the light diffuser element 18 which is incident thereupon. Upon receiving the portion of light within the distal isotropic tip 20 of the light-collecting pick-up fibers 19, the portion of light is conducted back along the fiber optic to a multichannel light measuring dosimeter (not shown). Thus, once the catheter is positioned and inner tube advanced until the light-collecting optical fiber tips 20 and light diffuser element 18 project beyond the distal end of the outer tube into the portion of the cavity distal to the balloon 16, the distal ends of the light-collecting pick-up fibers 19 bend outward away from the light diffuser element 18 to come to rest against the surrounding tissue (not shown). Light from a light source (not shown) may then be introduced into the proximal end of the optical waveguide 17 by suitable coupling means and conducted to the light diffuser element 18. The treatment light thus conducted by the fiber to the light diffuser element 18 at the distal end thereof is diffused outward by the light diffuser element 18 to illuminate the surrounding tissue. A portion of the illuminating light enters the light-collecting optical fiber tip 20 and is conducted to a light detector and dosimeter for monitoring.

While particular embodiments of the present invention have been illustrated and described, it would be obvious to those skilled in the art that various other changes and modifications can be made without departing from the spirit and scope of the invention. For example, it is advantageous to provide the inner and outer tubes with graduation marks such as the marks shown at 13 (FIG. 1) on the inner tube which enable the operator to measure relative positions of the tubes with respect to one another and for centering the distal tip of the catheter within a body cavity and deploying the pick-up fibers. It is therefore, intended to cover in the appended claims all such changes and modifications that are within the scope of this invention.

What we claim is:

1. A catheter for delivering treatment light to a target tissue within the body of an animal, said catheter comprising an elongate flexible cylindrical member having a non-invasive proximal end and an invasive distal end, said catheter further comprising:

(a) an elongate inner tube having a cylindrical outer surface substantially coextensive with said catheter and comprising an optical waveguide having a proximal end adapted to receive treatment light from a source of treatment light, a distal end and a light diffuser element in optical communication with said distal end of said optical waveguide, said optical waveguide being operable for conducting said treatment light to said light diffuser element and said light diffuser element being operable for delivering said treatment light to said target tissue; and (b) an elongate flexible outer tube coaxially mounted over said inner tube and having a proximal end, a distal end and an axial lumen therebetween, said axial lumen being dimensioned to slidingly accommodate said inner tube therewithin; and (c) at least one fiber optic attached to said outer surface of said inner tube, said at least one fiber optic having a proximal end and a distal end, said distal end of said at least one fiber optic extending beyond said distal end of said inner tube and being adapted to receive light from said light diffuser element; and (d) fiber optic bending means operable for bending said distal end of said at least one fiber optic in a radial direction when said distal end of said inner tube is slidingly advanced within said axial lumen and said distal end of said at least one fiber optic extends beyond said distal end of said outer tube.

2. The catheter of claim 1 wherein said diffuser element is operable for delivering diffuse light to said target tissue.

* * * * *